United States Patent [19]

Håkansson et al.

[11] Patent Number: 6,114,128
[45] Date of Patent: Sep. 5, 2000

[54] METHOD AND KIT FOR PREDICTING THE THERAPEUTIC RESPONSE OF A DRUG AGAINST A MALIGNANT TUMOR

[75] Inventors: Leif Håkansson; Annika Håkansson, both of Vikingstad; Bertil Gustafsson, Linköping, all of Sweden

[73] Assignee: Landstinget I Ostergotland, Linkoping, Sweden

[21] Appl. No.: 08/952,140

[22] PCT Filed: May 10, 1996

[86] PCT No.: PCT/EP96/02007

§ 371 Date: Nov. 10, 1997

§ 102(e) Date: Nov. 10, 1997

[87] PCT Pub. No.: WO96/35949

PCT Pub. Date: Nov. 14, 1996

[30] Foreign Application Priority Data

May 12, 1995 [SE] Sweden ................................. 9501782

[51] Int. Cl.[7] ........................ G01N 33/53; G01N 33/555; G01N 33/567; G01N 33/574
[52] U.S. Cl. ...................... 435/7.24; 435/7.21; 435/7.23; 436/63; 436/64
[58] Field of Search ................................ 435/7.21, 7.23, 435/7.24; 436/63, 64, 813

[56] References Cited

FOREIGN PATENT DOCUMENTS

WO 88/01385 2/1988 WIPO.
WO 92/08981 5/1992 WIPO.

OTHER PUBLICATIONS

Itoh, et al., *Cancer Immunol. Immunother.*, vol. 33, pp. 238–246, 1991.
Aebersold, P. et al., "Lysis of Autologous Melanoma Cells by Tumor–Infiltrating Lymphocytes: Association With Clinical Response", *Journal of the National Cancer Institute*, 83(13): 932–937 (Jul. 3, 1991).
Balch et al., "A Multifactorial Analysis of Melanoma: Prognostic Histopathological Features Comparing Clark's and Breslow's Staging Methods", *Ann. Surg.*, 188(6): 732–742 (Dec. 1978).
Balkwill, F., "Peptide Regulatory Factors", *The Lancet*: 1060–1063 (May 13, 1989).
Balkwill, F.R. et al., "Human Interfon Inhibits the Growth of Established Human Breast Tumors in the Nude Mouse", *Int. J. Cancer*, 30: 231–235 (1982).
Breard, J. et al., "A Monoclonal Antibody Reactive with Human Peripheral Blood Monocytes", *The Journal of Immunology*, 124(4): 1943–1948 (Apr. 1980).
Cosimi, A. et al., "Use of Monoclonal Antibodies to T–Cell Subsets for Immunologic Monitoring and Treatment in Recipients of Renal Allografts", *The New England Journal of Medicine*, 305(6): 308–314 (Aug. 6, 1981).
Creagan, E.T. et al., "Recombinant Interferons in the Management of Advanced Malignant Melanoma", *Am J. Clin Oncol (CCT)* 11(6): 652–659 (1988).

Eisenthal, A. et al., "Phenotypic and Functional Profile of Peripheral Blood Mononuclear Cells Isolated from Melanoma Patients Undergoing Combined Immunotherapy and Chemotherapy", *Cancer Immunol Immunther*, 37(6): 367–372 (Dec. 6, 1993).
Friedman, R. et al., "Interfeons with Special Emphasis on the Immune System", *Advances in Immunology*, 34: 97–140 (1983).
Gresser, I., "Biologic Effects of Interferons", *The Journal of Investigative Dermatology*, 95(6): 66S–71S (1990).
Gundersen, S. et al., "Interferon in Combination with Vinblastine in Advanced Malignant Melanoma", *Cancer*, 64: 1617–1619 (Oct. 15, 1989).
Hakansson, A. et al., "Tumor–Infiltrating Lymphocytes in Metastatic Malignant Melanoma and Response to Interferon Alpha Treatment", *British Journal of Cancer*, 74: 670–676 (1996).
Hansen, M. et al., "Tumor Thickness and Lymphocytic Infiltration in Malignant Melanoma of the Head and Neck", *The American Journal of Surgery*, 128: 557–561 (Oct. 1974).
Hersey, P. et al., "Immunohistological Relation Between DR Antigen Expression on Melanoma Cells and Infiltration by CD8+ T Cells", *Pathology*, 22: 133–139 (1990).
Hurwitz, P., "Spontaneous Regression of Metastatic Melanoma", *Annals of Plastic Surgery*, 26(4): 403–406 (Apr. 1991).
Hutchinson, G.H. et al., "Differential Immune Reactivity of Tumour–Intrinsic and Peripheral–Blood Lymphocytes Against Autoplastic Colurectal Carcinoma Cells," Br. J. Cancer, 44:396–402 (1981).
Jones, P. et al., "Prolonged Survival for Melanoma Patients with Elevated IgM Antibody to Oncofetal Antigen", *JNCI.* 66,(2): 249–254 (1981).

(List continued on next page.)

*Primary Examiner*—Yvonne Eyler
*Attorney, Agent, or Firm*—Merchant & Gould P.C.

[57] ABSTRACT

The present invention relates to a method of predicting the therapeutic response of a drug against a malignant tumour in a human patient, using a sample of a fine needle aspirate of the tumour from the patient. The method comprises the steps of identifying and estimating in the sample the number of cells belonging to one class of cells in relation to other cells in the sample, and comparing the estimation with a previously made analysis demonstrating correlation between the number of cells and parameters of the therapeutic response of the drug directed towards the tumour in human patients, the results of the comparison being indicative of the therapeutic response of the drug in human patient. A diagnostic kit comprises a mixture of enzymes rendering the sample of the tumour a single cell suspension, a first mixture of monoclonal antibodies directed towards tumour associated antigens on tumour cells in the single cell suspension, said antibodies having a first label, and a second mixture of two types of monoclonal antibodies directed towards two specific antigens on lymphocytes, said antibodies having a second and a third label, respectively.

7 Claims, No Drawings

OTHER PUBLICATIONS

Kang, S. et al., "Histologic Regression in Malignant Melanoma: An Interobserver Concordance Study", *Journal of Cutaneous Pathology*: 126–129 (1993).

Kirkwood, J. et al., "Interferon Alfa–2b Adjuvant Therapy of High–Risk Resected Cutaneous Meloma: The Eastern Cooperative Oncology Group Trial EST 1684", *Journal of Clinical Oncology*, 14(1): 7–17 (Jan. 1996).

Klein, E. et al., "Separation and Characteristics of Tumor–Infiltrating Lymphocytes in Man", *Contemporary Topics in Immunology*, (10): 79–107 (1980).

Knop, J., "Immunologic Effects of Interferon", *The Journal of Investigative Dermatology*, 95(6): 72S–74S (Dec. 1990).

Kornstein, M. et al., "Immunoperoxidase Localization of Lymphocyte Subsets in the Host Response to Melanoma and Nevi", *Cancer Research*, 43: 2749–2753 (Jun. 1983).

Larsen, T. et al., "A Retrospective Histological Study of 669 Cases Primary Cutaneous Malignant melanoma in Clinical Stage I", *Acta path. nicrobiol. scand. Sect. A*. 86: 523–530 (1978).

Legha, S., "Current Therapy for Malignant Melanoma", *Seminars in Oncology*, 16(1) Suppl 1: 34–44 (Feb. 1989).

McGovern, V. et al., "Lymphocyctic Infiltration and Survival in Malignant Melanoma", *Pathology of Malignant Melanoma*: 341–344 (1981).

McGovern, V.J. "Spontaneous Regression of Melanoma," *Pathology*, 7:91–99 (1975).

Miescher, S. et al., "Functional Properties of Tumor–Infiltrating and Blood Lymphocytes in Patients with Solid Tumors: Effects of Tumor Cells and Their Supernatants on Proliferative Responses of Lymphocytes", *The Journal of Immunology*, 136(5): 1899–1907 (Mar. 1986).

Miescher, S. et al., "Perferential Clonogenic Deficit of CD8–positive T–Lymphocytes Infiltrating Human Solid Tumors", *Cancer Research*, 48: 6992–6998 (Dec. 15, 1988).

Nind, A.P.P. et al., "Lymphocyte Anergy in Patients with Carcinoma", *Br. J. Cancer*, 28: 108–117 (1973).

Onishi, T. et al., "Assessment of Tumour–infiltrating Lymphocytes, Regional Lymph Node Lymphocytes and Peripheral Blood Lymphocytes and their Reaction to Interferon–gamma in Patients with Renal Carcinoma", *British Journal of Urology*, 67: 459–466 (1991).

Poppema, S. et al. "In situ Analysis of the Mononuclear Cell Infilrate in Primary Malignant Melanoma of the Skin", *Clin. exp. Immunol.*, 51: 77–82 (1983).

Riviere, Y. et al., "Direct Action of the Interferon and Inducers of Interferon on Tumor Cells in Athymic Nude Mice", *Cancer Research*, 43: 4596–4599 (Oct. 1983).

Ronan, S. et al., "Thin Malignant Melanomas With Regression and Metastases", *Arch Dermatol*, 123: 1326–1330 (Oct. 1987).

Rosenberg S., "The Immunotherapy and Gene Therapy of Gene Therapy of Cancer", *Journal of Clinical Oncology*, 10(2): 180–199 (Feb. 1992).

Rosenberg S., "A New Approach to the Adoptive Immunotherapy of Cancer with Tumor–Infiltrating Lymphocytes", *Science*, 233: 1318–1321 (Sep. 19, 1986).

Rosenberg S., "Use of Tumor–Infiltrating Lymphocytes and Interleukin–2 in the Immunotherapy of Patients with Metastatic Melanoma", *The New England Journal of Medicine*: 1676–1680 (Dec. 22, 1988).

Ruiter, D. et al., "Major Histocompatibility Antigens and Monoclear Inflammatory in Benign Nevomelanocytic Proliferations and Malignant Melanoma", *The Journal of Immunology*, 129(6): 2808–2815 (Dec. 1982).

Sondergaard, K. et al., "Partial Regression in Thin Primary Cutaneous Malignant Melanomas Clinical Stage I: A Study of 486 Cases", *Virchows Arch* [*Pathol Anat*] 408: 241–247 (1985).

Stanojevic–Bakic, N. et al., "T–Activin Therapy in Early Stage Melanoma Patients: In vitro and in vivo immunologic effect", *International Journal of Thymology*, 3(3): 265–272 (1995).

Tefany, F. et al., "Immunocytochemical Analysis of the Cellular Infiltrate in Primary Regressing and Non–Regressing Maliganant Melanoma", *The Journal of Investigative Dermatology*, 97(2): 197–202 (Aug. 1991).

Vose, B.M. et al., "Human Tumor–Infiltrating Lymphocytes: A Marker of Host Response", *Seminars in Hematology*, 22(1): 27–40 (Jan. 1985).

Vose, B.M. et al., "Mitogen Responsiveness and Inhibitory Activity of Mesenteric Lymph Node Cells", *Cancer Immunol Immunther*, 13: 105–111 (1982).

Vose, B.M. et al., "Specific and Non–Specific Lymphocyte Cytoxicity in Colon Carcinoma", *Br. J. Cancer*, 44: 846–855 (1981).

Whiteside, T. et al., "Tumor–Infiltrating Lymphocytes: Potential and limitations to their use for Cancer therapy", *Critical Reviews in Oncology/Hematology*, 12: 25–47 (1992).

METHOD AND KIT FOR PREDICTING THE THERAPEUTIC RESPONSE OF A DRUG AGAINST A MALIGNANT TUMOR

The present invention relates generally to a method of predicting the therapeutic response of a drug. More specifically, the invention relates to a method of predicting the therapeutic response of a drug directed towards a malignant tumour in a human patient, and to a diagnostic kit in order to enable the method to be applied routinely.

The importance of lymphocytes in the control by the immune system of malignant tumours as well as the necessary presence of these cells in tumours has been known for several decades. However, nobody has studied the presence of lymphocytes in tumours, using fine needle aspirates, in relation to immunotherapy and the effect of treating a disease with a successful outcome.

The outcome of a treatment of a patient with a specific drug against a malignant tumour is often unpredictable. Only about 15–20% of the patients respond to the medication of each type of treatment. The patients receiving the medication are subjected to an unnecessary suffering since adverse reactions often are obtained from the drug used. Mostly, the effect of the drug is not shown before 3–6 months of treatment. A drug for treatment of a malignant tumour is often expensive and a considerable cost reduction would be obtained if the drug used is effective. It would therefore be of great importance if patients with a high probability to respond could be identified before the onset of treatment.

For example, interferon-alpha (IFN-$\alpha$) has a documented activity, against malignant melanoma. Five to ten million units IFN-$\alpha$ three times weekly seems, at the cost of reasonable side effects, (Legha et al.) to be an optimal dose range. The treatment efficacy varies in different studies (Creagan et al., Gundersen, Legha et al.) and the over-all response rate (CR+PR) to IFN-$\alpha$ alone is only about 20% (Creagan et al., Legha et al.). It would therefore be a considerable improvement if patients with a high probability to respond to this treatment could be identified using predictive tests.

Besides having an antiproliferative activity (Balkwill et al,.Riviere et al.), the antitumour effect of IFN-$\alpha$ can be due to modulation of tumour cells, e.g. induction of 2,5-A synthetase or increased expression of cell surface proteins, MHC I and tumour associated antigens which are of importance for the immunological control of tumours. In addition, IFN-$\alpha$ modulates several immune functions (12 Friedman). There are still no firm data demonstrating which of these activities of IFN-$\alpha$ that is the most important one for the antitumour activity or if they all contribute.

As IFN-$\alpha$ modulates the activity of various cells in the immune system, e.g. activation of machrophages, NK-cells, cytotoxic T-cells and B-cell function (Friedman et al.), the therapeutic effect might depend on the immune status of the patients when IFN-$\alpha$ therapy is initiated.

Immune reactivity to malignant melanoma has been demonstrated as spontaneous regression (Mc Govern et al., Sondergaard et al., Ronan et al., Kang et al.), occurence of antibodies of prognostic significans against melanoma associated antigens and specific cytotoxic lymphocytes (Abershold et al.). Conflicting results have, however, been reported on the prognostic significance of lymphocytic infiltration in primary malignant melanoma. Some studies found a significantly better prognosis if the primary lesions had a prominent infiltration of lymphocytes (Hansen et al., Larsen et al.) whereas others found no such correlation (Balch et al.) Three studies also found a relation between tumour thickness and lymphocytic infiltration (Balch et al., Hansen et al., Larsen et al.). This discrepancy was further studied by Mc Govern et al. who found the lymphocytic infiltration at the base of the melanoma to be of prognostic significance in contrast to lymphocytic infiltration at the margins. These authors also found that the lymphocytic infiltration at the tumour base was reduced as tumour thickness increased. A reasonable strategy to treat malignant melanoma would therefore, based on the immune reactivity to this type of malignancy, be to enhance the anti-tumour immune reactivity by immunomodulating substances, such as interferons and Interleukin-2.

The purpose of the present invention is to produce a method of predicting the therapeutic response of a drug against a malignant tumour in a human patient, using a sample of a fine needle aspirate of said tumour from said patient. The method according to the invention is thus based on a direct diagnosis in the tumour of the accumulation of lymphocytes.

In order to achieve this purpose, the method according to the invention has been given the characterizing feature of claim 1.

The method of predicting the therapeutic response of a drug concerns patients with a regional as well as a generalised metastasis formation. It is also possible by means of the method according to the invention to predict and monitor immunotherapy.

MATERIAL AND METHODS

Patients Data.

This report includes 41 patients with metastatic malignant melanoma, 23 males and 18 females. Median age was 60 years (range 33 to 77) and Karnowsky performance status was 70 or more. All patients had histologically proven primary malignant melanoma and recurrences were cytologically proven before start of treatment. Twenty patients had regional metastases (20 lymphnode metastases), which in general were excised after 1 to 3 weeks of IFN-$\alpha$ treatment and 21 patients had systemic disease with the following metastatic sites: 2 cutaneous, 5 subcutaneous, 16 lymphnodes, 7 pulmonary, 3 bone, and 16 visceral (9 liver, 1 ovarian, 1 pancreatic, 1 vulvar, 1 adrenal gland and 3 spleen metastases). The number of metastatic sites were 1 in 7 patients, 2 in 5 patients, 3 in 4 patients, 4 in 1 patient and 5 or more in 4 patients. No patient had previously been treated except for surgical removal of primary lesions or metastases. Patients with symptoms of brain metastases were not included in this study.

Patients Evaluation.

Pre-treatment investigations included ECG, abdominal CT/US, chest X-ray, bone scintigraphy and blood samples for measurements of creatinine, bilirubin, alkaline phosphatase, alanine-aminotransferase, lactatdehydrogenase, alpha amylase, haemoglobin, white blood cells and thrombocytes.

Treatment Schedule.

In a pilot study including 12 patients (4 with regional disease and 8 with general metastases), IFN-$\alpha$ was given s.c. three days weekly at a dose of $10^6$ IU. In this pilot study it was decided to give Cyclophosfamide and Indometacin in addition to IFN-$\alpha$ in an attempt to enhance the therapeutic efficacy of IFN-$\alpha$. Patients were treated with cyclophosphamide at a dose of 300 mg/m² administered as i.v. bolus every three weeks and 6 of these patients were also treated with 50 mg of Indomethacin three times daily and 1 of the 6 was in addition given 400mg of Cimetidin twice daily. Tumour response was evaluated in patients with regional resectable disease after one to three weeks and in patients with distant metastases after one to three treatment cycles, one cycle being three weeks.

The pilot study was followed by a confirmatory study including 29 patients (16 with regional resectable disease and 13 with systemic disease) patients were treated with IFN-α alone, sc. at a dose of 10 milj. IU three times weekly in order to demonstrate the predictive value of CD4+ tumour infiltrating lymphocytes for the outcome of IFN-α treatment. In patients with regional resectable disease the treatment was given during one to three weeks before surgery and in the group with distant metastases treatment was given 3 weeks followed by one week without treatment. No other treatments were added in either group in the confirmatory study. Tumour respone was evaluated in patients with regional resectable metastases after the first cycle and in patients with distant metastases after one to three treatment cycles.

As no differences were found between the two studies regarding response rates or histopathological regression of tumour infiltrating inflammatory cells the results of them were added for the final analyses.

Monoclonal Antibodies.

CD4 (Leu-3a, Becton-Dickinson): The antigen is present on the helper T subset and in low density on monocytes and in the cytoplasm of monocytes and macrophages.

CD8 (Leu-2a, Becton-Dickinson): The antigen is present on cytotoxic/suppressor lymphocytes. The antigen is also expressed on some Leu-11+ (CD16) cytotoxic NK cells, on a subpopulation of Leu-7+ (HNK-1) cells (which do not have cytotoxic and NK activity), on some Leu-8+ cells (which participate in suppression of B-cell function), and on Leu-15+ (CD11b) cells which are associated with suppressor function.

CD11c: (M5, Becton-Dickinson): The antigen is present on monocytes and in low density on granulocytes and large granular lymphocytes in peripheral blood. It is also expressed on macrophages in normal lymphoid tissue, on Kuppfer cells in liver, and alveolar macrophages in lung tissue.

Fine Needle Aspiration of Metastases.

Usually seven to ten aspirations were taken from each tumour with a 0.1 mm hypodermic needle. No anesthesia was needed. The aspirate was smeared on a glass slide and was allowed to dry in air. At least two smears were then stained for conventional cytomorphology according to the May-Grunewald-Giemsa method. In cases without obvious melanin pigment in tumour cells the diagnosis of melanoma was confirmed with immunostaining for vimentin and protein S-100. Morphological signs of degeneration or necrosis were registered.

Immunological Staining of Fine Needle Aspirates.

The slides were air dried and then fixed for 5 minutes in aceton. After drying the slides were washed in phosphate buffered saline (PBS), pH 7.6, and incubated with monoclonal antibodies against CD4, CD8 and CD11c (see above) for 30 minutes. Mouse IgG (Sigma, Stockholm, Sweden) was used as negative control. After washing in PBS, the sections were incubated with rabbit anti-mouse immunoglobulin (Dakopatts Z 259) and incubated for 30 minutes, washed in TBS and incubated with the PAP mouse monoclonal antibody (Dakopatts, P 850) for 30 minutes. After washing in TBS, the slides were treated with Diaminobenzidin, DAB (Sigma, Stockholm, Sweden) in 3% $H_1O_2$ for 6 minutes and washed. The slides were counterstained in Mayers haematoxylin for 15 minutes, washed and mounted in Glycergel (Dakopatts, Sweden). All incubations were performed in a moist chamber.

Preparation of Tumour Biopsies and Immunological Staining of Tissue Sections.

Biopsies from resectable tumours were immediately snap frozen and stored at −70° C. until further processed. Frozen tissue sections, 6–7 μm thick, were fixed in acetone for 10 minutes and then air dried. They were washed in Tris-buffered saline (TBS), pH 7.6 for 5 min, incubated with primary antibodies CD4, CD8 and CD11c (see above) for minutes and then washed in TBS for 5 minutes. Mouse IgG (Sigma, Stockholm, Sweden) was used as negative control. The sections were then incubated with rabbit anti-mouse immunoglobulin (Dakopatts, Z 259) for 30 minutes, washed in TBS and incubated with the APAAP mouse monoclonal antibody (Dakopatts D 651) for 30 minutes. After washing in TBS and incubating with the alkaline phosphatase substrate (Naphtol AS-MX Phosphate 2mg (Sigma N4875), Dimethylformamide 0.2 ml, 0.1 M Tris buffer pH 8.2 9.8 ml, 1 M Levamisole 50 μl (Sigma L-9756) and Fast-Red TR salt 10 mg (Sigma F 1500) for 20 minutes, the sections were washed again in TBS. They were then counterstained in Mayers haematoxylin for 15 minutes and mounted in Glycergel (Dakopatts, Sweden). All incubations were performed in a moist chamber.

Evaluation of Mononuclear Cells.

Because of the often heterogenous distribution of infiltrating inflammatory cells, counting of cells per microscopic field was not performed. The overall occurence of each subset of these cells, in relation to the number of tumour cells, was instead scored as − (absent), + (sparse, low numbers), ++ (moderate), +++ (high) independently by two inverstigators. CD4+ cells scored as lymphocytes had small nuclei and sparse cytoplasm with distinct cell membrane. In contrast, CD4+ macrophages displayed large nuclei and abundant, generally faintly staining cytoplasm.

Criteria of Tumour Regression

Based on the description of regression in primary melanoma in other studies (Mc Govern et al., Kang et al., Sondergaard et al., Ronan et al.) the following critera of tumour regression were used in this study: 1. Low and variable density of tumour cells, particularly variation in density within the same tumour nodule, 2. Disorganisation of the architecture of the tumour with nests of remaining tumour cells surrounded by stromal tissue. The occurence of regressive areas varies from no signs of regression to almost complete destruction of the tumour with only few remaining tumour cells.

The occurence of regressive changes of the tumours used in this study of patients with resected metastatses were estimated to be less than 25% (slight regression), 25–75% and more than 75% (marked regression).

Statistical Methods.

The difference in distribution of inflammatory cells between patients with tumour response and progressive disease was analysed using the chi-square test.

EXAMPLE 1.

Treatment Efficacy.

Two groups of patients were studied, those with resectable, regional metastases and those with general metastases. In the latter group the effect of IFN-α treatment was determined as reduction in tumour size. As the main objective of this study was to analyse the importance of tumour infiltrating inflammatory cells for the anti-tumour effect of IFN-α, significant tumour regression (more than 25%) in patients with mixed responses and regressions not fullfilling the criteria for partial remission were registered and used in the following analyses. Among patients with general metastases 11 out of 21 patients had reduction in tumour size. One had a complete remission, 4 partial remission, 3 had a reduction of measurable tumours between 25–50%, 3 had a mixed response, and 10 patients had progressive disease.

Patients with regional, resectable metastases were treated with IFN-α for only one to three weeks due to the importance of not delaying surgery. This is of course too short a time to allow an adequate determination of the treatment efficacy based on measurement of the tumour size only, thus the determination of therapeutic effect in this group was based on the occurence of tumour regression in the histopathological examination of the tumour biopsies. Metastases with ongoing regression were generally permeated by CD4+ and CD8+ lymphocytes as well as CD11c+ machro-phages.

Histopathological criteria for signs of spontaneous regression of malignant melanoma has been described in primary tumours. Based on such criteria (described above) nine patients with regional metastases had marked histopathological regression of the resected metastases and 11 patients had only slight regressive changes.

As no differences regarding tumour regression—determined as reduction in size or occurence of histopathological regressive changes—were found between the pilot study and the confirmatory study the patients of these studies were combined in the analyses below. The results obtained in the few (five) patients treated with IFN-α for one week did not seem to differ from the results after 2–3 weeks of treatment, thus, all patients were combined in the following analyses.

Subsets of Tumour Infiltrating Mononuclear Cells (MNC).

The fine needle aspirates were obtained from lymphnode, subcutaneous and liver metastases. The occurence of tumour infiltrating mononuclear cells in these aspirates were studied before initiation of IFN-α treatment. The number and distribution of various subsets of of mononuclear cells in the aspirates from the different metastases showed considerable individual variation (Table 1).

TABLE 1

Occurence of tumour infiltrating CD4+, CD8+ and CD11c+ inflamatory cells in fine needle aspirates from patients with regional and systemic disease before initiation of IFN-α treatment.

| Number of infiltrating cells | CD4 | | | CD8 | | | CD11C | | |
|---|---|---|---|---|---|---|---|---|---|
| | Low | Moderate | High | Low | Moderate | High | Low | Moderate | High |
| Regional disease | 6 | 4 | 10 | 9 | 7 | 3 | 6 | 8 | 5 |
| Systemic disease | 10 | 7 | 4 | 14 | 4 | 2 | 6 | 4 | 6 |

Before treatment high numbers of CD4+ cells were found in metastases from 10 out of 20 patients with regional metastases. In all patients with high numbers of CD4+ cells more than 50% of these cells showed morphologic characteristics of lymphocytes. In contrast, in tumours with low numbers of these cells, CD4+ macrophages were more abundant than CD4+ lymphocytes in 2 out of 6 patients. In patients with moderate numbers of CD4+ cells macrophages were more abundant than lymphocyes in 2 out of 4 patients.

In patients with general metastases high numbers of CD4+ cells were found in 4 out of 21 patients before treatment, a result which is significantly different from the frequency found in patients with regional disease (P<0.05). In all of these patients more than 50% of the CD4+ cells showed morphologic characteristics of lymphocytes. In aspirates from patients with low numbers of CD4+ cells macrophages were more abundant than lymphocytes in 1 out of patients. In patients with moderate numbers of CD4+ cells macrophages were shown to be more abundant than lymphocytes in out of 7 patients.

In patients with regional disease CD4+ cells predominated over CD8+cells in 7 out of 19 patients. In 10 patients there were no predominance of either subsets and in 2 CD8+ cells predominated over CD4+ cells.

High numbers of CD11c+ macrophages were found in 4 out of 19 patients with regional disease before treatment. In the group with general disease high numbers were found in 5 out of 20 tumours.

The occurence of inflammtory cells in fine needle aspirates and in biopsies after IFN-α treatment were compared in 20 patients. Even if IFN-α might influence the recruitment of these cells there was in general a very good correlation. Lower numbers of CD4+ cells in tissue sections compared to aspirates were found in only 3 out of 20 patients. One of these 3 patients was a responder. All biopsies contained varying degrees of remnants of normal lymph node, which might explain this discrepancy. Alternatively a down regulation might have occurred during IFN-α treatment. Two biopsies showed an increase of CD4+ cells compared to aspirates, one of them was a responder. The size of lymph node metastases seems to be of some guidance as to the prescence of remaining normal lymph node. Remnants of normal lymph node was found in 7 out of 13 lymph node metastases less than 20 mm in diameter in contrast to only 2 out of 7 in lymph node metastases of larger size.

Correlation to Response to IFN-α Treatment.

The occurence of inflammatory cells in relation to the therapeutic effect of IFN-α is shown in Table 2 for patients with general metastases and in Table 3 for patients with regional, resectable metastases. Obviously, there is a very good correlation between anti-tumour effect and the presence of CD4+ lymphocytes in both these groups of patients. The occurence of these cells in aspirates from responding patients with distant metastases differs significantly from that of patients with progressive tumours (p=0.007). A similar difference is found also for patients with regional metastases, with more CD4+ lymphocytes in metastases showing marked histopathological regressive changes after IFN-α treatment compared to patients with only slight or no regressive changes in the metastases (p=0.077). Surprisingly, there was no correlation between the occurence of CD8+ or CD11c+ cells and response to IFN-α treatment, neither in regional nor in general disease.

TABLE 2

Number of tumour infiltrating CD4+, CD8+ and CD11c+ inflamatory cells in patients with inoperable systemic metastatic disease according to clinical effect of IFN-α treatment

| Number of infiltrating cells | CD4 Therapeutic effect | | | CD8 Therapeutic effect | | | CD11C Therapeutic effect | | |
|---|---|---|---|---|---|---|---|---|---|
| | R | MR | PD | R | MR | PD | R | MR | PD |
| Low | 1 | 0 | 9 | 4 | 2 | 8 | 3 | 1 | 3 |
| Moderate | 4 | 2 | 1 | 1 | 1 | 2 | 3 | 1 | 4 |
| High | 3 | 1 | 0 | 2 | 0 | 0 | 1 | 1 | 3 |

TABLE 3

Number of tumour infiltrating CD4+, CD8+ and CD11c+ inflamatory cells in patients with regional disease according to histopathological regression after IFN-α treatment.

| Number of infiltrating cells | CD4 Marked histopat. | CD4 Slight regr. | CD8 Marked histopat. | CD8 Slight regr. | M5 Marked histopat. | M5 Slight regr. |
|---|---|---|---|---|---|---|
| Low | 1 | 5 | 3 | 6 | 2 | 4 |
| Moderate | 1 | 3 | 3 | 4 | 4 | 4 |
| High | 7 | 3 | 2 | 1 | 2 | 3 |

According to the present invention a good correlation was obtained between the occurrence of a specific class of cells and the therapeutic response to a drug against a tumour. In the example given this correlation was obtained with the helper T subset and the therapeutic benefit of IFN-α. In patients with regional disease 7 out of 10 patients with high numbers of these cells in fine needle aspirates achieved marked histopathological tumour regression. In contrast, in patients with low numbers of cells of this subset 5 out of 6 patients achieved only a slight regression of their tumours. In the group with distant metastases 10 out of 11 of those with moderate or high infiltration of cells of this subset in the tumours achieved tumour regression. In contrast, among patients with low infiltration of these cells 9 out of 10 had progressive disease. Based on these results there seems to be a need for cells of this subset infiltrating the tumours before start of treatment with IFN-α to make the treatment successful. Thus, the degree of infiltration of these cells seems to be a useful predicitve test for chosing patients suitable for this therapy.

In order to simplify and facilitate the diagnostic techniques with a fine needle aspirate of a tumour from a patient the use of a diagnostic kit is applied. An example of such a kit is given below.

A single cell suspension the fine needle aspirate is prepared by suspending the aspirate in a solution containing a mixture of the enzymes collagenase, hyaluronidase and DNAase. A mixture of monoclonal antibodies directed towards tumour associated antigens on tumour cells and labelled with one type of fluorochrome (type A) is added to the cell suspension thus obtained. Then a mixture of monoclonal antibodies directed towards CD3 (a T-lymphocyte marker) and CD4 antigens on lymphocytes is added, i.e. anti-CD3 antibodies labelled with a fluorochrome type B and anti-CD4 antibodies labelled with a fluorochrome type C. Such a double staining is used in order to identify CD4+ lymphocytes and avoid the counting of CD4+ monocytes/macrophages. The numbers of tumor cells and double stained lymphocytes are then determined by means of flow cytometry. A high ratio CD4+ lymphocytes/tumour cells will according to the invention identify responders to immunotherapy.

References.

Abershold, P. Lysis of autologous melanoma cells by tumour infiltrating lymphocytes: Association with clinical response. J Nat Cancer Inst. 1991;83:932–937.

Balch, C. M. A multifactorial analysis of melanoma: Prognostic Histopathological features comparing Clark's and Breslow's staging methods. Ann Surg. 1978;188:732–742.

Balkwill, F. Human interferon inhibits the growth of established human breast tumours in the nude mouse. Int J Cancer. 1982;30:231–235.

Breard, J. A monoclonal antibody reactive with human peripheral blood monocytes. J Immunol. 1980;124:1943.

Cosimi, A. Use of monoclonal antibodies to T-cell subsets for immunological monitoring and treatment in recipients of renal allografts. N Eng J Med. 1981;305–308.

Creagan, E. Recombinant Interferons in the management of Advanced malignant melanoma. Am J Clin Oncol. 1988;11:652–659.

Friedman, R. M. Interferons with special emphasis on the immune system. Adv. Immunol. 1983;34:97–140.

Gundersen, S. Interferon in combination with Vinblastin in advanced malignant melanoma. A phase I–II study. Cancer. 1989;64:1617–1619.

Hansen, M. G. Tumour thickness and lymphocytic infiltration in malignant melanoma of the head and neck. Am J Surg. 1974;12:8557–8561.

Hersey, P. Immunohistological relation between DR antigen expression on melanoma cells and infiltration by CD8+ T cells. Pathology. 1990;22:133–139.

Hutchinson, G. H. Differential immune reactivity of tumour intrinsic and peripheral blood lymphocytes against autoplastic colorectal carcinoma cells. Br J Cancer. 1981;44:396–402.

Kang, S. Histologic regression in malignant melanoma: an interobserver concordance study. J. Cutan. Pathol. 1993;126–129.

Kirkwood, J. A randomized controlled trial of high-dose IFN-alpha-2b for high risk melanoma: The ECOG trial EST 1684. Proc Am Soc Clin Oncol 1993;12:390.

Klein, E. Separation and characteristics of tumour infiltrating lymphocytes in man. Immunobiology. 1980;10:79–107.

Kornstein, M. J. Immunoperoxidase localization of lymphocyte subsets in the host respons to melanoma and nevi. Cancer Res. 1983;43:2749–2753.

Larsen, T. A retrospective histological study of 669 cases of primary cutaneous malignant melanoma in clinical stage I. ACTA Pathol. Microbiol. Scand. 1978;86:523–530.

Legha, S. Current therapy for malignant melanoma. Sem Oncol. 1989;16:34–44.

Mc Govern, V. J. Lymphocytic infiltration and survival in malignant melanoma. Pathology malignant melanoma, A. B. Ackerman (ed.), Masson Publishing. 1981;341–344.

Mc Govern, V. J. Spontaneous regression of melanoma. Pathology. 1975;7:91–99.

Miescher, S. Functional properties of tumour infiltrating and blood lymphocytes in patients with solid tumours: Effects of tumour cells and their supernatants on proliferative responses of lymphocytes. J Immunol. 1986;136:1899–1907.

Miescher, S. Preferential clonogenic deficit of CD8+ T lymphocytes infiltrating human solid tumours. Cancer Res.

Nind, A. P Lymphocyte anergy in patients with carcinoma. Br J Cancer. 1973;28:108–117.

Nind, A. Lymphocyte anergy in patients with carcinoma. Br J Cancer. 1973;28:108–117.

Onishi, T. Assessment of tumour infiltrating lymphocytes, regional lymph node lymphocytes and peripheral blood lymhocytes and their reaction to Interferon-gamma in patients with renal cell carcinoma. Br J Urology. 1991;67:459–466.

Poppema, S. In situ analysis of the mononuclear cell infiltrate in primary malignant melanoma of the skin. Clin Exp immunol. 1983;51:77–82.

Riviere, Y. Direct action of Interferon and inducers of interferon on tumour cells in athymic nude mice. Cancer Res. 1983;43:4596–4599.

Ronan, S. Thin malignant melanomas with regression and metastases. Arch. Dermatol. 1987;123:1326–1330.

Rosenberg, S. A. A new approach to the adoptive immunotherapy of cancer with tumour infiltrating lymphocytes. Science. 1986;233:1318–1321.

Rosenberg, S. A. The immunotherapy and gene therapy of cancer. J Clin Oncol. 1998;10:188–199.

Ruiter. Major histocompatibility antigens and mononuclear inflammatory infiltrate in benign nevomelanocytic proliferations and malignant melanoma. J Immunol. 1982;129:2808–2815.

Sondergaard, K. Patrial regression in thin primary cutaneous melignant melanomas clinical stage I. Virchows Arch. 1985;408:241–247.

Tefany, F. Immunocytochemical analysis of the cellular infiltrate in primary regressing and non-regressing malignant melanoma.

Vose, B. M. Human tumour infiltrating lymphocytes: A marker of host response. Sem. Haematol. 1985;22:27–40.

Vose, B. M. Mitogen responsiveness and inhibitory activity of mesenteric lymph node cells. Conditioned medium containing T cell growth factor reverses suppressor function. Cancer Immunol Immunother. 1982;13:105–111.

Vose, B. M. Specific and non-specific lymphocyte cytotoxicity in colon carcinoma. Br J Cancer. 1981, 44:846–855.

What is claimed is:

1. Method of predicting the therapeutic response of a drug against a malignant tumour in a human patient, using a sample of a fine needle aspirate of said tumour from said patient, characterized in that the method comprises the steps of:

identifying tumour infiltrating mononuclear cells in said sample and estimating therein the number of tumour infiltrating mononuclear cells in relation to the number of tumour cells; and comparing said estimation with a previously made analysis demonstrating correlation between the number of tumour infiltrating mononuclear cells in relation to the number of tumor cells and tumour regression of said drug directed towards said tumour in human patients;

wherein an accumulation of tumor infiltration mononuclear cells is indicative of a therapeutic response of said drug in said human patient.

2. Method as in claim 1, characterized in that said identification and estimation of cells is performed by means of immunological staining.

3. Method as in claim 1, characterized in that said drug is an immunomodulating drug.

4. Method as in claim 1, characterized in that said cells are lymphocytes.

5. Method as in claim 4, characterized in that said lymphocytes are CD4+.

6. Method as in claim 1, characterized in that said-tumour is a metastatic malignant melanoma and said drug is interferon-alfa.

7. Method as in claim 2, characterized in that said immunological staining is performed with monoclonal antibodies.

* * * * *